(12) United States Patent
Meeks et al.

(10) Patent No.: US 8,896,825 B2
(45) Date of Patent: Nov. 25, 2014

(54) OPTICAL INSPECTOR

(71) Applicants: Steven W. Meeks, Palo Alto, CA (US);
Rusmin Kudinar, Fremont, CA (US);
Hung P. Nguyen, Santa Clara, CA (US)

(72) Inventors: Steven W. Meeks, Palo Alto, CA (US);
Rusmin Kudinar, Fremont, CA (US);
Hung P. Nguyen, Santa Clara, CA (US)

(73) Assignee: Zeta Instruments, Inc., San Jose, CA (US)

( * ) Notice: Subject to any disclaimer, the term of this patent is extended or adjusted under 35 U.S.C. 154(b) by 56 days.

(21) Appl. No.: 13/757,154

(22) Filed: Feb. 1, 2013

(65) Prior Publication Data

US 2014/0218722 A1   Aug. 7, 2014

(51) Int. Cl.
| | | |
|---|---|---|
| *G01N 21/00* | (2006.01) | |
| *G02B 26/12* | (2006.01) | |
| *G02B 26/10* | (2006.01) | |
| *G01N 21/01* | (2006.01) | |

(52) U.S. Cl.
CPC ............. *G01N 21/01* (2013.01); *G02B 26/125* (2013.01); *G02B 26/10* (2013.01)
USPC ....................................................... 356/237.1

(58) Field of Classification Search
CPC ................................................ G01N 21/9501
USPC ....................................................... 356/237.1
See application file for complete search history.

(56) References Cited

U.S. PATENT DOCUMENTS

| | | | |
|---|---|---|---|
| 4,626,101 A | 12/1986 | Ogawa et al. | |
| 5,399,866 A * | 3/1995 | Feldman et al. | ........... 250/458.1 |
| 5,822,128 A * | 10/1998 | Sekine | ........................ 359/650 |
| 6,069,690 A | 5/2000 | Xu et al. | |
| 6,624,884 B1 | 9/2003 | Imaino et al. | |
| 6,686,602 B2 | 2/2004 | Some | |
| 6,704,435 B1 | 3/2004 | Imaino et al. | |
| 6,791,099 B2 | 9/2004 | Some et al. | |
| 7,907,269 B2 | 3/2011 | Meeks | |
| 2005/0046848 A1* | 3/2005 | Cromwell et al. | ............ 356/417 |
| 2006/0102839 A1* | 5/2006 | Bhaskar et al. | ............... 250/310 |
| 2007/0138392 A1* | 6/2007 | Cole | .......................... 250/341.1 |
| 2008/0037134 A1* | 2/2008 | Boef et al. | .................... 359/648 |
| 2009/0250628 A1 | 10/2009 | Mano | |
| 2012/0049085 A1 | 3/2012 | Sappey et al. | |

OTHER PUBLICATIONS

Zhiqiang Li, Thomas Ryan, Proc. of SPIE vol. 7231. Light-Emitting Diodes: Materials, Devices, and Applications for Solid State Lighting XIII, Edited by Klaus P. Streubel, Heonsu Jeon, Li-Wei Tu, Proc. of SPIE vol. 7231, 72310P, 2009.

* cited by examiner

*Primary Examiner* — Tarifur Chowdhury
*Assistant Examiner* — Md Rahman
(74) *Attorney, Agent, or Firm* — Imperium Patent Works; Mark D. Marrello (57) ABSTRACT

An optical inspector includes a radiating source, a time varying beam reflector, a telecentric scan lens, a first and second lens, a field stop, and a detector. The radiating source irradiates a first position of on the time varying beam reflector with a source beam. The time varying beam reflector directs the source beam to the telecentric scan lens, which in turn directs the source beam to a sample. The first lens focuses scattered radiation from the sample to generate multiple scan lines at a first focal plane. The field stop is positioned at the first focal plane to block one or more scan lines at the first focal plane. The scan line not blocked by the field stop propagates to the second lens. The second lens de-scans the scan line and generates a point of scattered radiation at a second focal plane where the detector input is located.

17 Claims, 12 Drawing Sheets

TOP VIEW

OPTICAL INSPECTOR

LIGHT EMITTING DIODE (LED) WAFER
(CROSS-SECTIONAL VIEW)

FIG. 1

OPTICAL INSPECTOR
FIG. 2

FIG. 3
OPTICAL INSPECTOR
SIDE VIEW

OPTICAL INSPECTOR
FIG. 4

SCATTERED RADIATION FROM DIFFERENT SURFACES

FIG. 5

OPTICAL INSPECTOR
FIG. 6

OPTICAL INSPECTOR WITH ACHROMATIC LENSES

FIG. 7

OPTICAL INSPECTOR WITH ACHROMATIC LENSES
AND FIELD STOP

FIG. 8

SCATTERED RADIATION FROM EACH SURFACE AT
THE CAMERA LENS FOCUS

FIG. 9

SCATTERED RADIATION FROM EACH SURFACE AT THE CAMERA LENS
FOCUS WITH FIELD STOP BLOCKING BOTTOM SURFACE SCATTER

FIG. 10

SAMPLE DEFECT MAPPING

FIG. 11

OPTICAL INSPECTION FLOWCHART
FIG. 12

OPTICAL INSPECTION FLOWCHART

FIG. 13

OPTICAL INSPECTOR

TECHNICAL FIELD

The described embodiments relate generally to detecting wafer defects and more particularly to detecting defects in a transparent or opaque wafer.

BACKGROUND INFORMATION

Light Emitting Diodes (LEDs) are typically produced by an epitaxial deposition of alloys of gallium nitride (GaN) on a transparent wafer substrate such as a sapphire. Many different types of defects may appear on either the substrate or the epitaxial layer. Some of these defects may be cracks in the sapphire which can then appear in the GaN layer, growth defects in GaN layer, pits, particles and stains from contaminates. In many cases, LED manufacturers will deposit GaN layers on patterned sapphire substrates (PSS). PSS serves to improve the light extraction efficiency by reducing the amount of light which is guided by total internal reflection. Manufacturers also desire to detect defects in the PSS since this will result in additional GaN growth defects or reduced light extraction efficiency.

Figure 1:
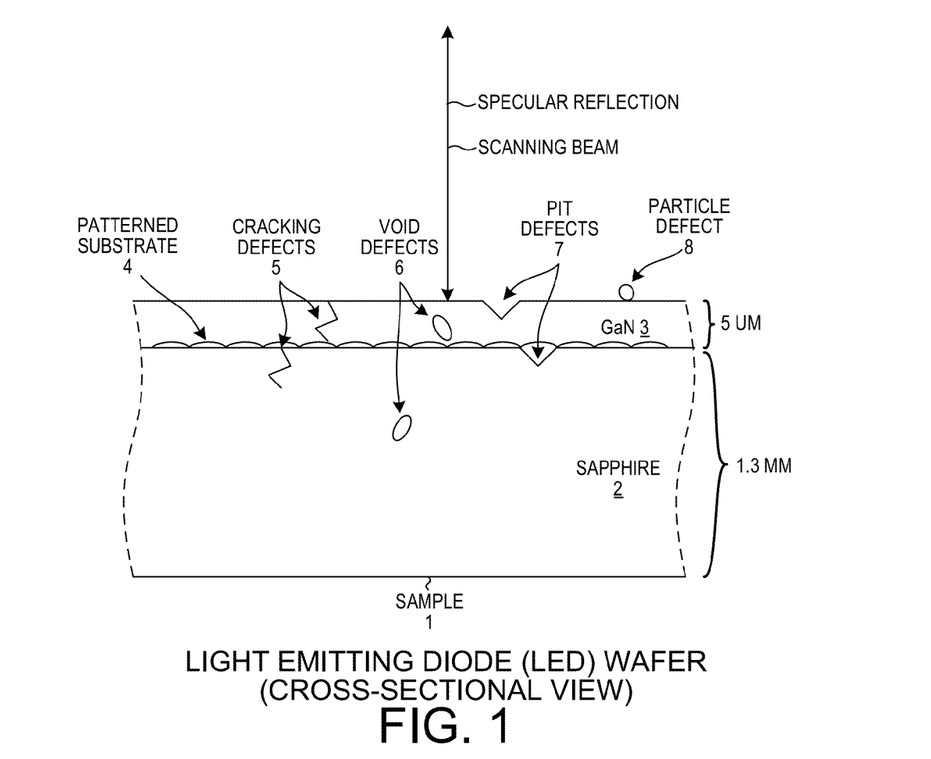
FIG. 1 is a cross-sectional diagram of a Light Emitting Diode (LED) wafer.

The inspection of transparent substrates is complicated by the difficulty of separating the scattered light from the top and bottom surfaces. A diagram of a transparent substrate is shown in FIG. 1. FIG. 1 shows a 1.3 mm thick sapphire substrate with a 5 micron thick GaN layer which is produced by epitaxial growth. It is desired to inspect the top surface of the GaN or bare sapphire for defects and to exclude the scattered light signal from the bottom surface of the sapphire. In the prior art, Meeks (U.S. Pat. No. 7,907,269) describes a method to separate top and bottom surface scattered light. Meeks teaches the use of either an oblique or normal laser wherein bottom surface scattered light is separated by means of a beam block with a pinhole.

SUMMARY

A surface optical inspector directs a source beam onto a surface of a sample and in response measures various types of radiation from the sample. The types of radiation include specular reflection, near specular scattered radiation, and scattered radiation. The measured information is processed to determine the total reflectivity of the sample, the surface slope of the sample, scattered radiation intensity, near specular scattered radiation intensity and determine whether defects are present in the sample.

In a first novel aspect, the surface optical inspector includes a time varying beam reflector, a radiating source that irradiates a first position on the time varying beam reflector with source radiation, a telecentric scan lens that directs the source radiation from the time varying beam reflector onto a sample, a separating minor that receives reflected radiation from the sample, a first detector that receives a first portion of the reflected radiation from the separating minor, and a second detector that receives a second portion of the reflected radiation. The second portion of the reflected radiation does not reflect off the separating mirror.

In a second novel aspect, the time varying beam reflector is a rotating polygon, the sample is a wafer or disc, the first portion of the reflected radiation includes specular reflection, the second portion of the reflected radiation includes near specular scattered radiation, the radiating source is a laser, the first detector is a bi-cell photodiode detector, and the second detector is a photomultiplier tube detector.

In a third novel aspect, the surface optical inspector includes a radiating source that irradiates a first position of a time varying beam reflector, a telecentric lens that directs the radiation reflected by the time varying beam reflector onto a sample, a lens that receives scattered radiation from the sample, a field stop located at the focal plane of the lens (the field stop blocks a first portion of the scattered radiation), a de-scan lens located after the focal plane of the camera lens that receives a second portion of the scattered radiation not blocked by the field stop, and a detector located at the focal plane of the de-scan lens.

In a fourth novel aspect, the time varying beam reflector is a rotating polygon, the sample is a wafer or disc, the scattered radiation includes a top surface scattered radiation generated from the top surface of the sample and a bottom surface scattered radiation generated from the bottom surface of the sample, the first lens is a camera lens, the field stop is opaque and blocks the top or bottom surface scattered radiation, the de-scan lens is a pair of achromatic lenses, the radiating source is a laser, and the detector is a photomultiplier tube detector.

Further details and embodiments and techniques are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

DETAILED DESCRIPTION

Reference will now be made in detail to background examples and some embodiments of the invention, examples of which are illustrated in the accompanying drawings. In the description and claims below, relational terms such as "top", "down", "upper", "lower", "top", "bottom", "left" and "right" may be used to describe relative orientations between different parts of a structure being described, and it is to be understood that the overall structure being described can actually be oriented in any way in three-dimensional space.

FIG. 1 is a cross-sectional diagram of a Light Emitting Diode (LED) wafer (i.e. a sample). The wafer includes a sapphire substrate 2 on which a gallium nitride layer (GaN) 3 has been epitaxially grown. During the fabrication of both the sapphire substrate 2 and the GaN layer 3, unwanted defects can be produced. These unwanted defects include cracking defects 5, void defects 6, pit defects 7, and particle defects 8. These defects may occur within the sapphire substrate 2 or the GaN layer 3. These defects result in undesirable results such as reduced operating life of the resulting LED device, non-functionality of the resulting LED device, and degraded performance (light efficiency) of the resulting LED device. Further, some LED wafers include a patterned substrate 4 to improve light extraction efficiency. The patterned substrate 4 in a LED wafer may also suffer defects during fabrication. It is valuable to a LED manufacturer to detect these defects before additional resources are spent developing a product that will not function properly due to wafer level defects.

It is noted herein, the example of a GaN LED is used for exemplary use only. This disclosure is not limited to the detection of defects in a GaN LED. Further, the example of a sapphire substrate is used for exemplary use only. This disclosure is not limited to the detection of defects in sapphire wafers. Rather, this disclosure is applicable to all transparent, semi-transparent, and opaque wafers or discs regardless of the specific material constituting the wafer/disc or the end device to be manufactured with the developed wafer/disc.

Figure 2:
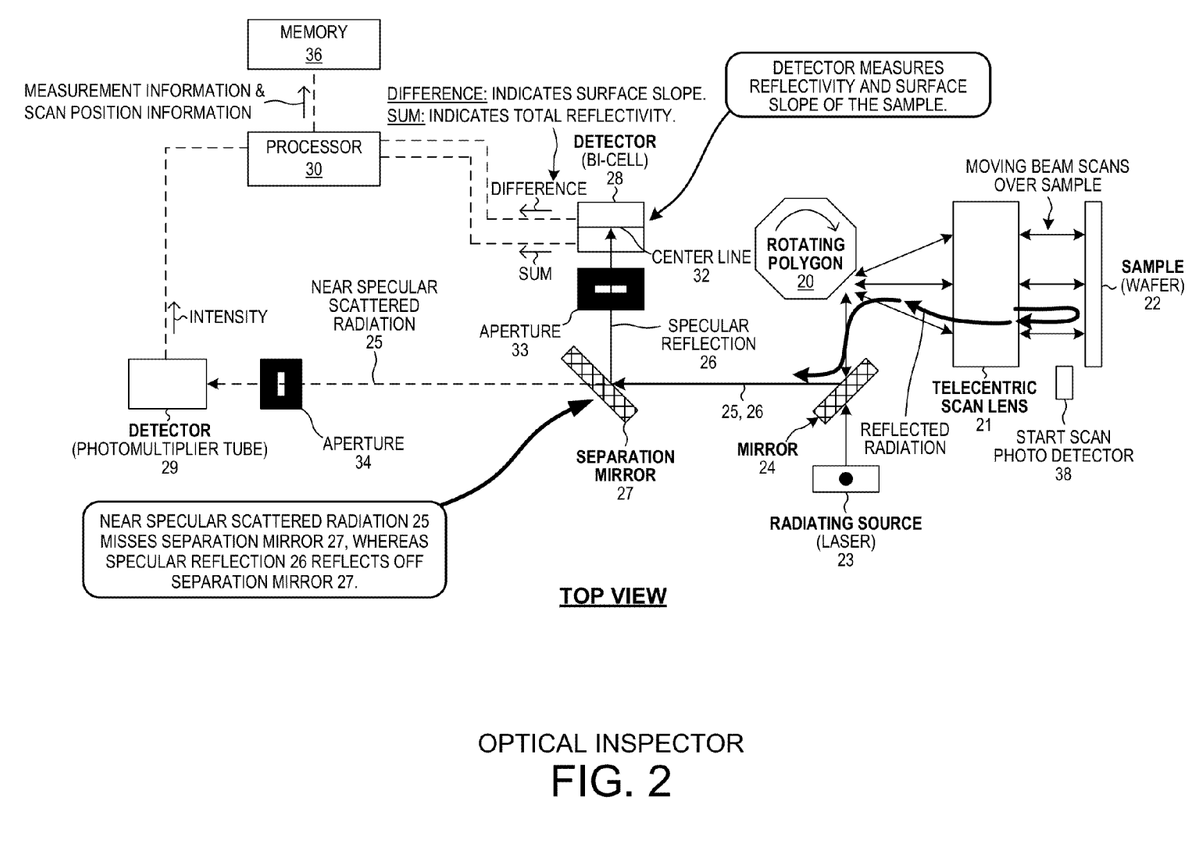
FIG. 2 is a top-view diagram of an optical inspector.

FIG. 2 is a top view diagram of an optical inspector. The optical inspector includes a rotating polygon 20, a telecentric scan lens 21, a radiating source 23, a mirror 24, a separation mirror 27, a bi-cell photo detector 28, and a photomultiplier tube detector 29. It is noted herein, the use of rotating polygon is exemplary. Any time varying beam reflector, such as a resonant galvanometer, a rotating double sided mirror, or acousto-optic beam deflector can be utilized as well.

The radiating source 23 irradiates rotating polygon 20 with a source beam. In one example, the radiating source 23 is a laser. The source beam is directed by the rotating polygon 20 to a first location on the telecentric scan lens 21. The angle at which the source beam approaches the telecentric scan lens 21 depends upon the angle of rotation of the rotating polygon 20 when the source beam contacts the rotating polygon 20. However, regardless of the angle at which the source beam approaches the telecentric scan lens 21, the telecentric scan lens 21 directs the source beam to a sample 22 at an angle that is substantially normal to the surface of the sample 22. In one example, the sample is the LED wafer 1 shown in FIG. 1.

The source beam directed, at a substantially normal angle, to the sample 22 generates a reflection of the source beam. A first portion of the reflected source beam is specular reflection. A second portion of the reflected source beam is near specular scattered radiation. Specular reflection is the mirror-like reflection of light from a surface, in which light from a single incoming direction is reflected into a single outgoing direction (in adherence with the law of reflection). Near specular scattered radiation is light which is scattered (or deflected) by defects to a region which is just outside the profile of the specular beam. Measuring both the specular reflection and the near specular scattered radiation allows the detection of defects which may not be visible in the specular reflection alone.

The specular reflection 26 and the near specular scattered radiation 25 are reflected back to the telecentric scan lens 21. The telecentric scan lens 21 directs the specular reflection 26 and the near specular scattered radiation 25 to the rotating polygon 20. The rotating polygon 20 directs the specular reflection 25 and near specular scattered radiation 26 back toward the radiating source 23. At this point, separating the source beam with the reflected light would be impractical if both the source beam and the reflected beams were traveling in the same space. To avoid this problematic situation, the radiating source 23 is placed at a location at an offset from the central axis 31 of the telecentric scan lens 21. The central axis 31 is illustrated in the side view portion of FIG. 3. As shown in the side view diagram of FIG. 3, when the radiating source 23 is offset from the central axis 31, the beam approaches the sample 22 at a small non-normal angle, thus resulting in the reflected beam reaching the telecentric scan lens 21 at a position symmetrically opposite the central axis 31. This allows the use of the first mirror 24 to direct the reflected beams away from the radiating source 23 without altering the source beam radiating from the radiating source 23.

The specular reflection 26 and the near specular scattered radiation 25 are directed by mirror 24 toward separation mirror 27. Separation mirror 27 directs the specular reflection 26 to the bi-cell photo detector 28. Simultaneously, near specular scattered radiation 25 travels above and/or below separation mirror 27 toward photomultiplier tube detector 29.

Figure 3:
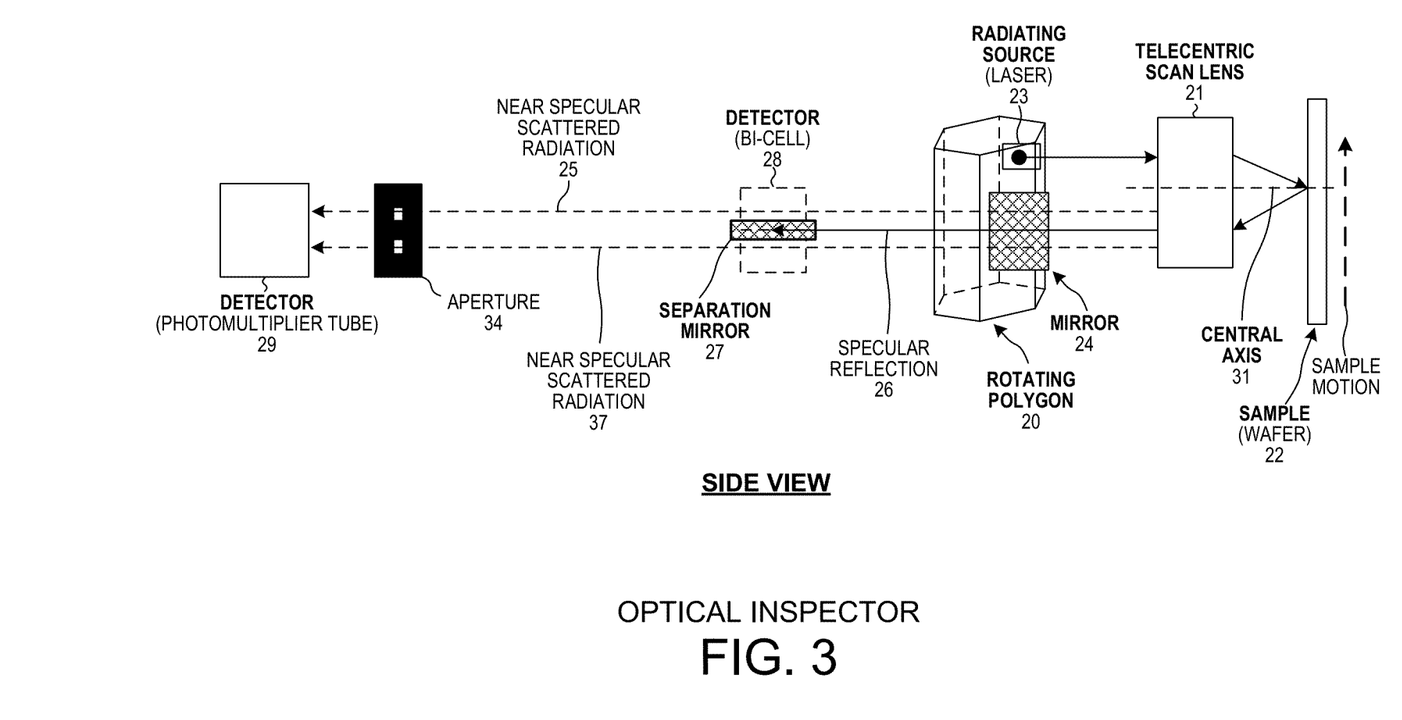
FIG. 3 is a side-view diagram of a first example of an optical inspector.

In one example, as shown in FIG. 3, separation mirror 27 is placed at the exact location of the specular reflection 26 beam and separation mirror 27 has a height that is approximately equal to the beam width of the specular reflection beam. As such, a portion of the reflected beam that travels at a height greater than the height of the top edge of separation mirror 27 continues to photomultiplier tube detector 29. Likewise, any portion of the reflected beam that travels at a height less than the height of the bottom edge of separation mirror 27 continues to the photomultiplier tube detector 29. These portions of the reflected beam that travel above and below separation mirror 27 are labeled near specular scattered radiation 25, 37 in FIG. 3.

Figure 4:
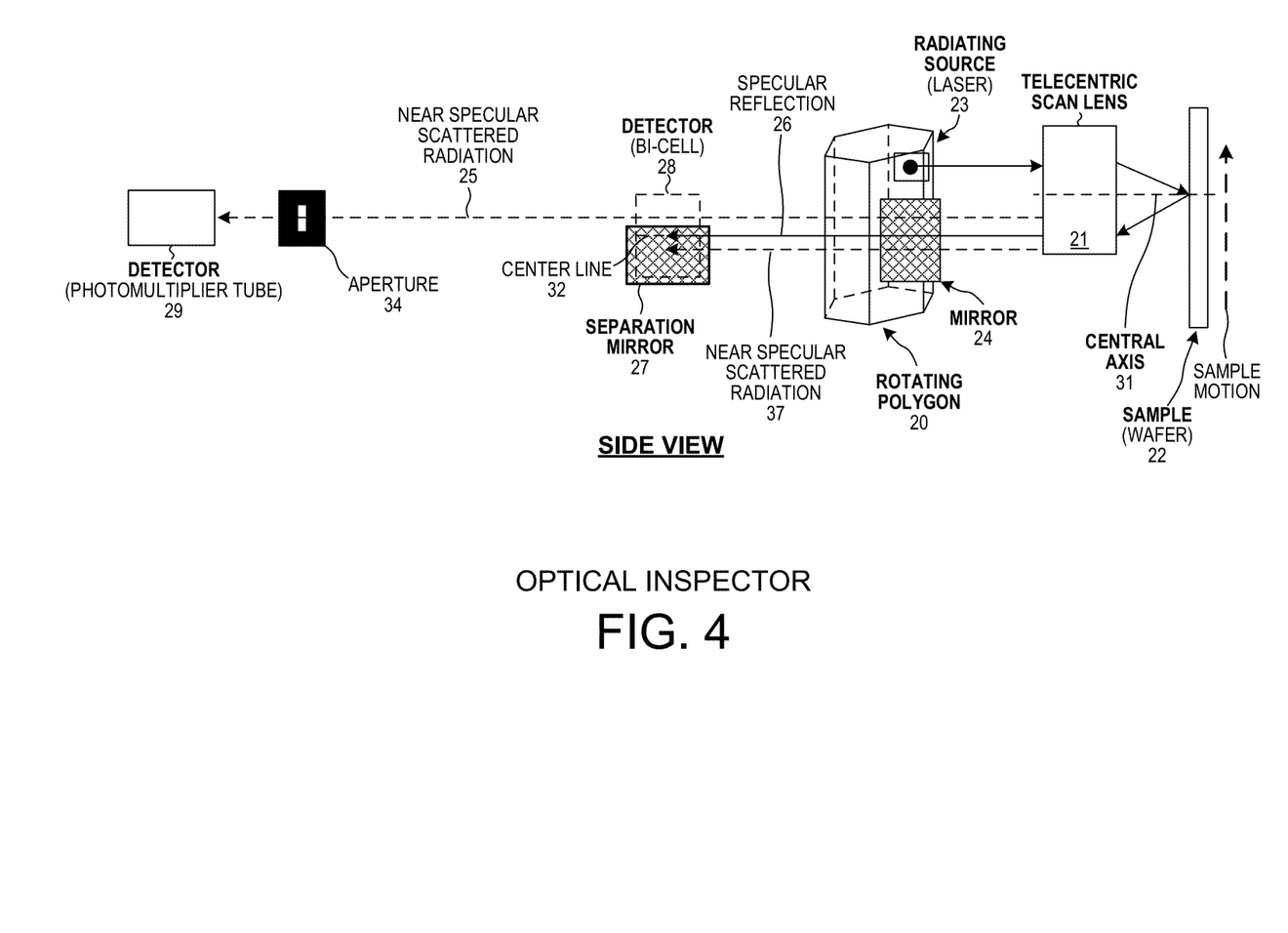
FIG. 4 is a side-view diagram of a second example of an optical inspector.

In a second example, as shown in FIG. 4, separation mirror 27 is placed at the location of the specular reflection 26, separation mirror 27 has a height that is greater than the beam width of the specular reflection beam, and the top edge of separation mirror 27 is aligned to the top edge of specular reflection beam. As such, a portion of the reflected beam that travels at a height greater than the height of the top edge of separation mirror 27 continues to the photomultiplier tube 29. Alternatively, any portion of the reflected beam that travels at a height less than the height of the bottom edge of specular reflection beam is directed toward bi-cell detector 28. The portion of the reflected beam that travels above separation mirror 27 is near specular scattered radiation 25. The portion of the reflected beam that is reflected by separation mirror 27 is near specular scattered radiation 37.

In another example, an aperture 33 is included between separation mirror 27 and bi-cell detector 28. Aperture 33 serves to block any near specular scattered radiation directed toward bi-cell detector 28 from separation mirror 27. In an alternative example, aperture 34 is included between mirror 24 and photomultiplier tube detector 29. Aperture 34 serves to block any non-near specular scattered radiation directed toward photomultiplier tube detector 29 from mirror 24.

The bi-cell detector 28 is located such that the specular reflection 26 should irradiate the bi-cell detector 28 on the center line 32 (as shown in FIGS. 2, 3 and 4) between the two photodiodes included in the bi-cell detector 28. In the event that the surface slope (the "micro-waviness") of the sample is not normal to the source beam, the resulting specular reflection 26 will deviate from the center line 32. A deviation from the center line 32 will cause a greater amount of the specular reflection 26 to irradiate one of the two photodiodes in the bi-cell detector 28. In response, the bi-cell detector 28 will output an increased difference value indicating a change in the slope of the sample 22 surface. A negative difference value indicates a slope varying in a first direction. A positive difference value indicates a slope varying in a second direction. The slope measured is the surface slope of the sample 22 in direction perpendicular to the optical scan line. Regardless of the deviation of the specular reflection 26 from the center line 32, the bi-cell detector 28 will output a sum value indicating the reflectivity of the sample 22.

In another example, a processor 30 is also included in the top surface optical inspector shown in FIG. 2. The processor 30 receives the an intensity output signal from the photomultiplier tube detector 29, a difference output signal from bi-cell detector 28, and a sum output signal from bi-cell detector 28. In response, processor 30 determines whether defects are present at the scan location on the sample 22.

The processor may also communicate with a motor controlling rotating polygon 20. The processor may increase or decrease the rate of rotation of the rotating polygon 20. For example, when switching from using a high-bandwidth detector to a low-bandwidth detector, it may be required that the rate of rotation of the rotating polygon 20 be decreased. Alternatively, when switching from using a low-bandwidth detector to a high-bandwidth detector, it may be necessary to increase the rate of rotation of the rotating polygon 20.

In another example, memory 36 is included in the top surface optical inspector shown in FIG. 2. Memory 36 stores information output by processor 30. (i.e. defect information, or defect indicator information). Memory 36 also stores location information indicating the location on the sample which was scanned to measure the defect information or defect indicator information. Defect information is a status as to whether the scanned location on the sample contains a defect or not. Defect indicator information includes various measurements from the scanned location on the sample (i.e. surface slope, total reflectivity, intensity of scattered radiation).

The amount of near specular scattered light which is collected is limited by the size of the polygon mirror facets and the size of the minor 24. The near specular scattered radiation passes above the separation mirror 27 and is incident on the photomultiplier tube (PMT) detector. The PMT measures the intensity of the near specular scattered light. Localized defects will appear as variations (increases or decreases) in the near specular scattered light signal.

In one example, the scan of the sample is done with the polygon rotating at a high speed and the data sampling of the bi-cell detector is run at approximately 16 MHz with the radiating source running at full intensity. Since the rotating polygon can rotate at high speeds, an entire 100 mm diameter sample can be measured in about ten seconds.

In another example, the rotating polygon begins to spin upon power up of the device and continues to spin until the entire device is powered off. The constant spinning of the rotating polygon during operation is beneficial in that spin-up and spin-down delay time is eliminated during regular operation. As shown in FIGS. 3 and 4, the sample is moved in the direction shown by a precision stage (not shown) to make a map of the entire sample surface. In one embodiment, shown in FIG. 2 the optical inspector includes a start of scan photodetector 38 which is placed at the edge of the scan line and serves to trigger the acquisition of data sampling when the scanned beam passes over the detector 38.

This above process is repeated as the sample 22 is moved underneath the optical inspector. A precision stage wafer mover controls the movement of the sample 22 during the inspection process. In one example, the processor 30 outputs defect inspection data which is logged along with the sample scan location. The number and location of defects on the sample will determine the disposition of the sample. In one example, depending upon the location and type of defect, some portions of the sample may be useful and others portions of the sample may be discarded. In another example, if the sample has many defects then the entire sample may be discarded.

It is noted herein, that the bi-cell detector 28 is of exemplary use in this disclosure. One skilled in the art will readily realize that the bi-cell detector 28 may be replaced with various multi-cell detectors to achieve the utility of the present invention.

It is noted herein, that the use of a photomultiplier tube detector 29 is of exemplary use in this disclosure. One skilled in the art will readily realize that the photomultiplier tube detector 29 may be replaced with other light sensing detectors such as a silicon photodetector to achieve the utility of the present invention.

Prior art, Meeks (U.S. Pat. No. 7,907,269) uses a pinhole and a beam block to separate top and bottom surface scatter. The difficulty with the prior art lies in the difficulty in aligning the pinhole. Therefore, there is a need for a new apparatus, method, and means for separating top surface and bottom surface scatter from transparent substrates without the use of a pinhole.

Figure 5:
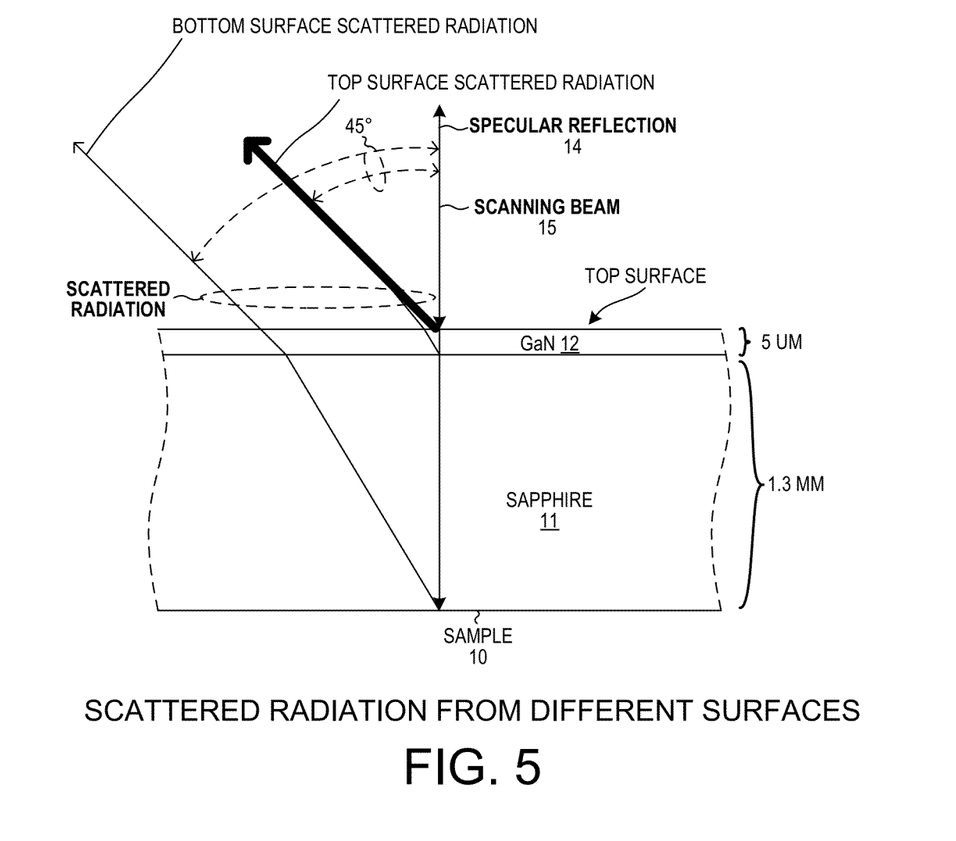
FIG. 5 is a diagram of scattered light rays reflected from the various surfaces within a LED wafer.

FIG. 5 is a diagram of scattered light rays from the top and bottom surfaces of a sample 10 (i.e wafer). The exemplary wafer illustrated is similar to the wafer illustrated in FIG. 1. The sample 10 (i.e. the wafer) contains two layers: a GaN layer, and a sapphire substrate. As discussed in FIGS. 2 and 3, a scanning beam 15 irradiates the sample surface. In response, a specular reflection 14 is generated, as is scattered radiation from the top and bottom of each layer. Given that the GaN layer is relatively thin (i.e. on the order of five micrometers) the scattered radiation generated from the top surface of the GaN layer and the scattered radiation generated from the bottom surface of the GaN layer are located in nearly the same space, and therefore are very difficult to separate. However, the sapphire layer is relatively thick (i.e. on the order of 1.3 millimeters). Thus, thus the scattered radiation generated from the top and bottom surfaces of the GaN layer and the scattered radiation generated from the bottom surface of the sapphire substrate have a greater degree of separation and therefore are easier to separate. This provides the opportunity to observe scattered radiation from only one surface once the scattered radiation from the other surface is properly blocked. In a first example, one may observe only the top surface scattered radiation once the bottom surface scattered radiation is properly blocked. In a second example, one may observe only the bottom surface scattered radiation once the top surface scattered radiation is properly blocked.

Figure 6:
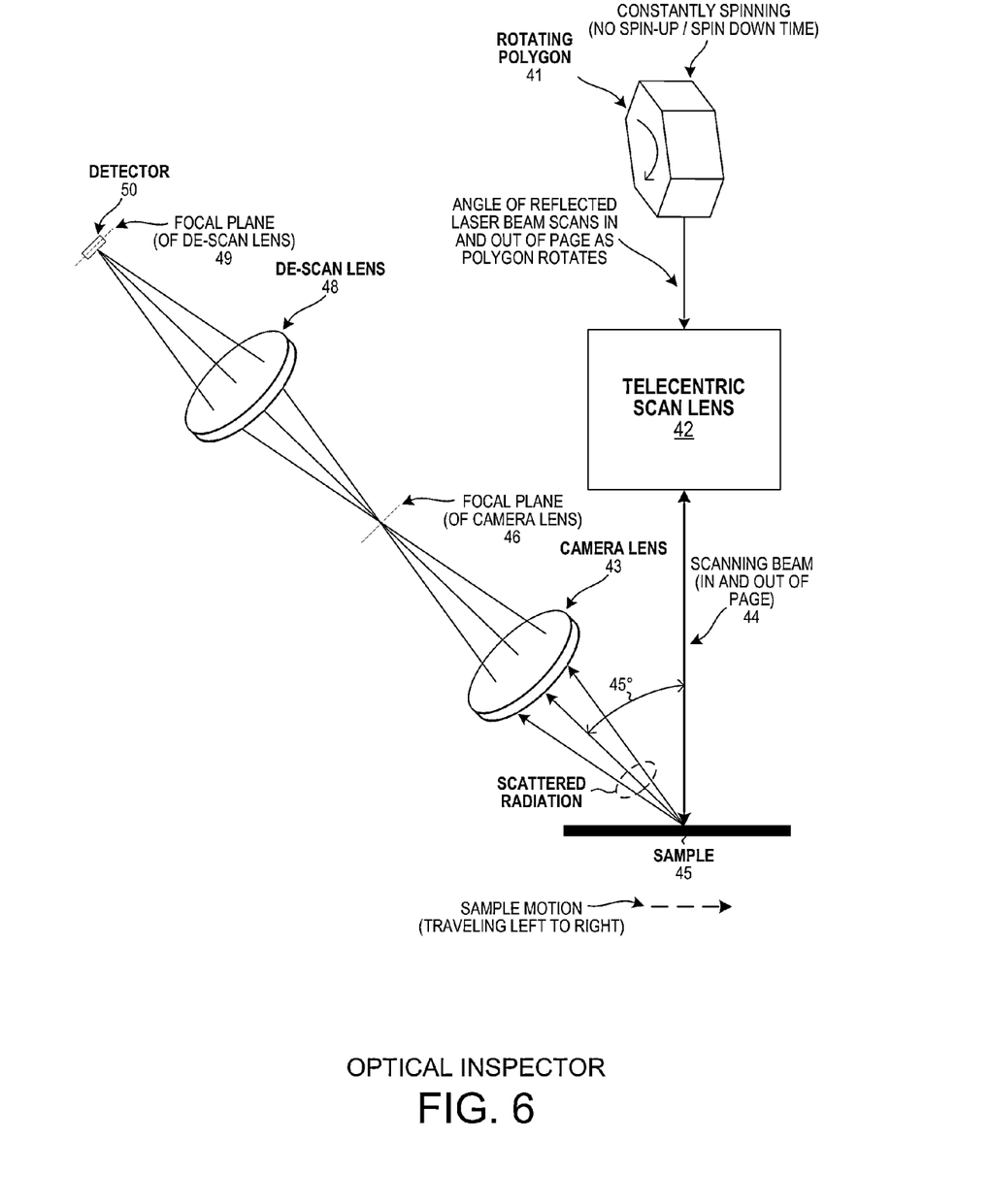
FIG. 6 is a front-view diagram of an optical inspector.
Figure 9:
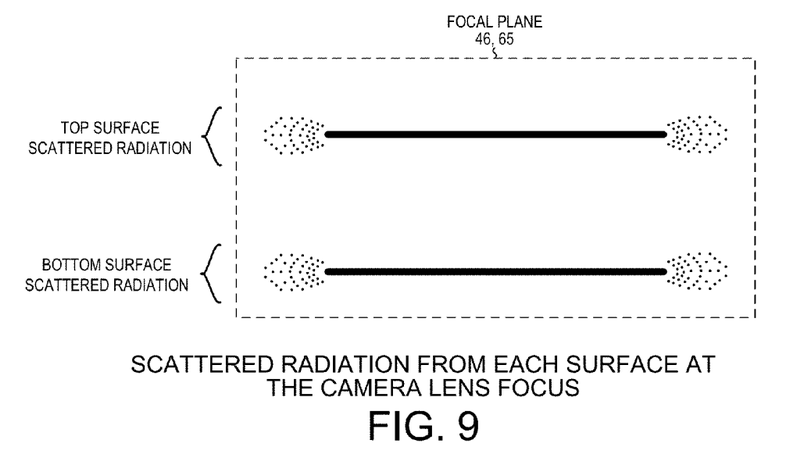
FIG. 9 is a diagram of scattered light at the first focal planes illustrated in FIGS. 6 and 7.

FIG. 6 is a diagram of an optical inspector. The optical inspector includes a rotating polygon 41, a telecentric scan lens 42, a camera lens 43, a de-scan lens 48, and a detector 50. A radiation source irradiates the rotating polygon 41 which directs a moving source beam with varying angular direction onto telecentric scan lens 42. Telecentric scan lens 42 redirects the source beam with varying angular direction to an angle substantially normal to sample 45. As shown in FIG. 5, the source beam causes a scattered radiation to be radiated from sample 45. Camera lens 43, located at an oblique angle from the plane of incidence of the source beam, receives a portion of the scattered radiation as shown in FIG. 6. As the source beam scans across the surface of sample 45, the scattered radiation from the sample forms a scan line at the focal plane 46 of camera lens 43. As discussed regarding FIG. 5, the scattered radiation from the top surface of the GaN layer generates a scan line very close to the scan line generated from the top surface of the sapphire layer. The focused scattered radiation at focal plane 46 is illustrated in FIG. 9. The scattered radiation propagates to de-scan lens 48. At de-scan lens 48 the scattered radiation is focused. De-scan lens 48 focuses the scattered radiation into a stationary spot of light at focal plane 49. The stationary spot of light generated at focal plane 49 contains scattered radiation from the top GaN surface, the top sapphire surface, and the bottom sapphire surface. Because the GaN layer is only about five microns thick, it is not possible to separate the scattered radiation of the top GaN surface from the scattered radiation from the top sapphire substrate surface; however, it is possible to separate the scattered radiation from the bottom surface of the sapphire substrate from the scattered radiation of the top surface.

In one example, the angle of inclination of the camera lens with respect to the plane of incidence of the scanned beam is approximately forty five degrees. The oblique angle of incidence allows the camera lens to separate the scattered radiation from the top and bottom surfaces of the transparent wafer. The amount of separation between the top and bottom surface is determined by the wafer thickness, the angle of incidence, and the index of refraction of the transparent wafer.

It is noted herein that the de-scan lens 48 shown in FIG. 6 may actually be a pair of positive achromatic lenses with the most highly curved side of each achromatic lens facing the other achromatic lens. It is also noted that camera lens 43 shown in FIG. 6 may be replaced with one of a Cooke triplet lens, a plano-convex lens, an aspheric lens, or an achromatic lens.

Figure 7:
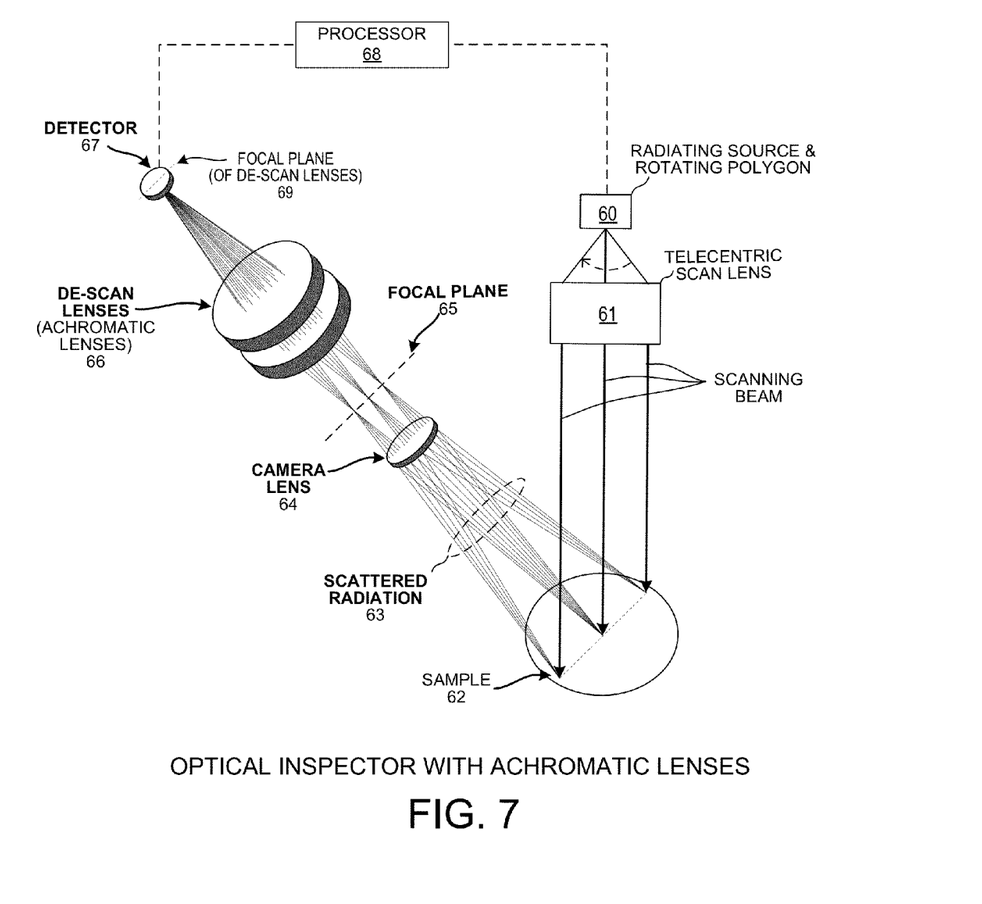
FIG. 7 is a side-view diagram of an optical inspector with achromatic lenses.

FIG. 7 is a diagram of a optical inspector with achromatic lenses. The optical inspector includes a radiating source and rotating polygon 60, a telecentric lens 61, a camera lens 64, a pair of de-scanning achromatic lenses 66, and a detector 67. The radiation source irradiates the rotating polygon which directs a moving source beam with varying angular direction onto telecentric scan lens 61. Telecentric scan lens 61 redirects the source beam with varying angular direction to an angle substantially normal to sample 62. As shown in FIG. 5, the source beam causes scattered radiation to be radiated from the sample. Camera lens 64, located at an oblique angle from the plane of incidence of the source beam, receives a portion of the scattered radiation. As the source beam scans across the surface of sample 62, the scattered radiation from the sample 62 forms a scan line at the focal plane 65 of camera lens 64. As discussed regarding FIG. 5, the scattered radiation from the top surface of the GaN layer generates a scan line very close to the scan line generated from the top surface of the sapphire layer. The scattered radiation continues to de-scan lenses 66. De-scan lenses 66 focus the scattered radiation into a circular spot at focal plane 69. The single spot of light generated at focal plane 69 contains scattered radiation from the top GaN surface, the top sapphire surface, and the bottom sapphire surface. Because the GaN layer is only about five microns thick, it is not possible to separate the scattered radiation of the top GaN surface from the scattered radiation from the top sapphire substrate surface; however, it is possible to separate the scattered radiation from the bottom surface of the sapphire substrate from the scattered radiation of the top surface.

In one example, the optical inspector also includes a processor 68. Processor 68 communicates with either detector 67 or a motor controlling the rate of rotation of rotating polygon 60, or both. In one example, detector 67 communicates a signal indicating the intensity of the light detected by detector 67 to processor 68. The processor 68 then determines if defects are present in the scanned area of the sample based upon the signal received from detector 67. In another example, processor 68 sends a signal to a motor controlling the rotating polygon 60. The signal sent to the motor causes the motor to increase or decrease the rate at which the rotating polygon rotates.

It is noted herein that camera lens 64 shown in FIG. 7 may be replaced with one of a Cooke triplet lens, a plano-convex lens, an aspheric lens, or an achromatic lens.

In another example, the angle of inclination of the camera lens with respect to the plane of incidence of the scanned beam is approximately forty five degrees. The oblique angle of incidence allows the camera lens to separate the scattered light from the top and bottom surfaces of the transparent wafer. The amount of separation between the top and bottom surface is determined by the wafer thickness, the angle of incidence, and the index of refraction of the transparent wafer.

Figure 8:
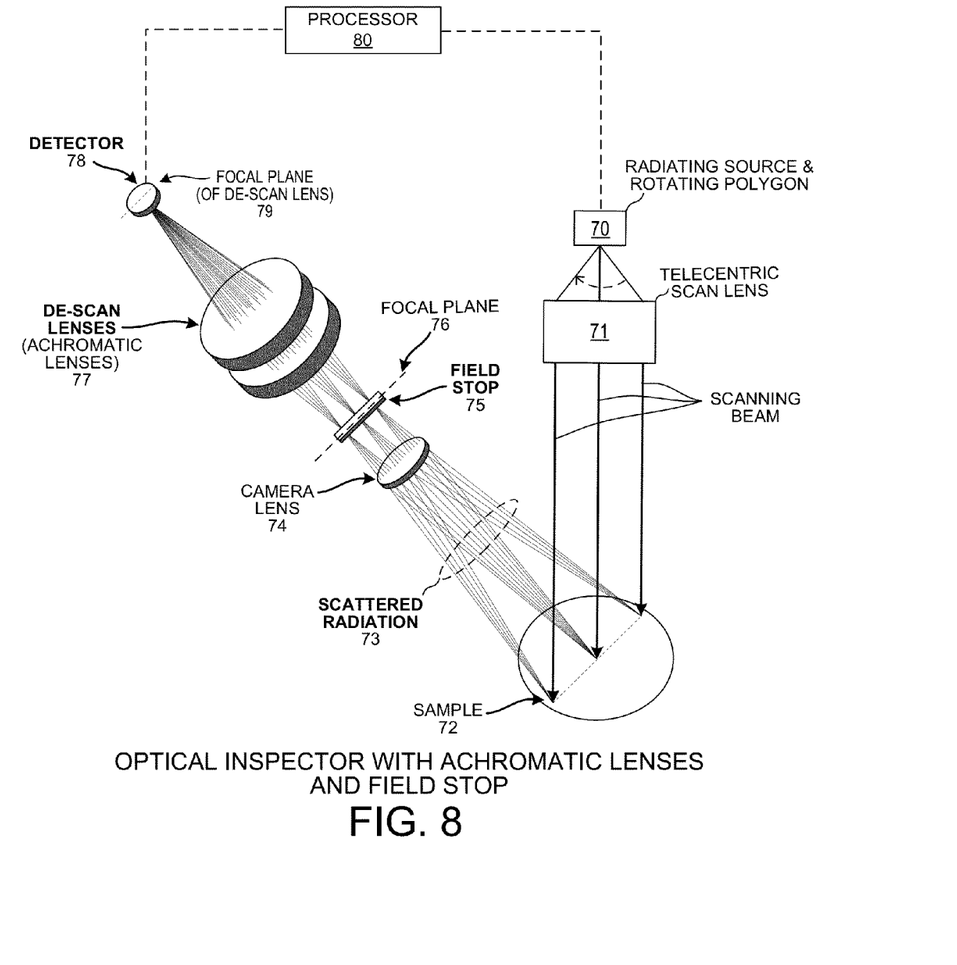
FIG. 8 is a side-view diagram of an optical inspector with achromatic lenses and a field stop.
Figure 10:
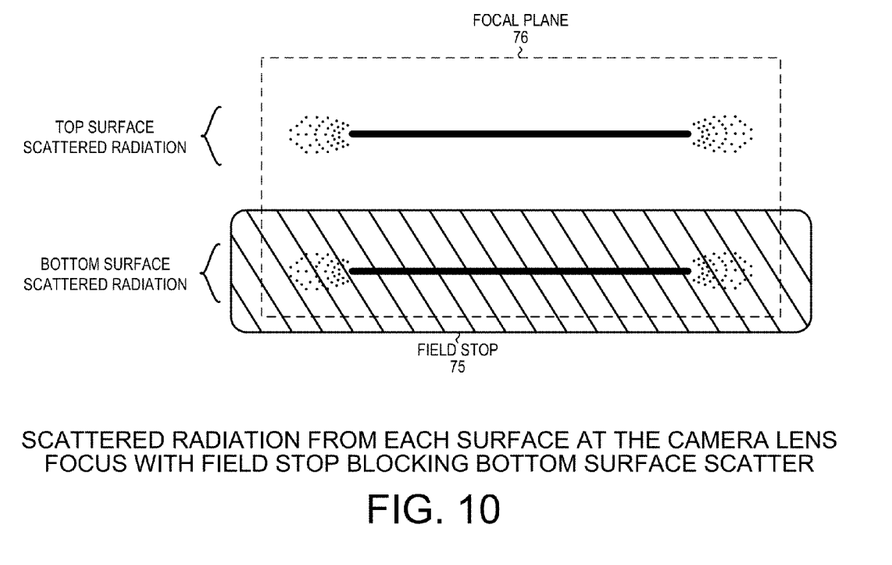
FIG. 10 is a diagram of scattered light at the first focal plane illustrated in FIG. 8.

FIG. 8 is a diagram of an optical inspector with achromatic lenses and field stop. The optical inspector includes a radiating source and rotating polygon 70, a telecentric lens 71, a camera lens 74, a field stop 75, a pair of de-scanning achromatic lenses 77, and a detector 78. The radiation source irradiates the rotating polygon 70 which directs a moving source beam with varying angular direction onto telecentric scan lens 71. Telecentric scan lens 71 redirects the source beam with varying angular direction to an angle substantially normal a sample 72. As shown in FIG. 5, the source beam causes scattered radiation to be radiated from sample 72. Camera lens 74, located at an oblique angle from the plane of incidence of the source beam, receives a portion of the scattered radiation. As the source beam scans across the surface of sample 72, the scattered radiation from the sample 72 forms a scan line at the focal plane 76 of camera lens 74. As discussed regarding FIG. 5, the scattered radiation from the top surface of the GaN layer generates a scan line very close to the scan line generated from the top surface of the sapphire layer. The scan lines generated by the scattered reflection at focal plane 76 are illustrated in FIG. 10. Field stop 75 is oriented such that the scan lines generated from the bottom surface scattered radiation is blocked by the field stop 75, while the top surface scattered radiation is not blocked by the field stop 75. This type of field stop simply blocks all the radiation below the top edge of the field stop. A pinhole is not needed since the bottom surface scatter radiation only appears as a line located below (or above) the top surface scatter. After passing the field stop the scattered radiation is still in the form of a rapidly moving small spot. This would appear to the human eye as a line of scattered light. However, if one places a lens or lenses after the focal point of the camera lens, the line of scattered radiation can be transformed to a stationary circular spot. In the embodiment shown in FIG. 8, the de-scanning lens is actually a pair of identical achromatic lenses with their most curved surfaces facing each other. This type of de-scanning lens transforms the linear scan into an angular scan which converges to produce a stationary circular spot at a fixed location. In one example, the location of the stationary circular spot is where a photomultiplier tube (PMT) detector is placed for the detection of the scattered radiation. Due to the field stop 75 shown in FIG. 8, the scattered radiation detected by the PMT in FIG. 8 is from the top surface only.

It is noted herein that de-scan lenses 77 of FIG. 8 may be replaced with a camera lens, a Cooke triplet lens, a plano-convex lens, or a aspheric lens. It is also noted herein that camera lens 74 shown in FIG. 8 may be replaced with one of a Cooke triplet lens, a plano-convex lens, an aspheric lens, or an achromatic lens.

In one example, field stop 75 is rectangular and opaque. The top surface scattered radiation not blocked by field stop 75 propagates to de-scan lenses 77. At de-scan lenses 77 the top surface scattered radiation is de-scanned. De-scan lenses 77 focus the top surface scattered radiation into a circular spot at focal plane 79. The circular point of light generated at focal plane 79 only contains scattered radiation from the top surface scattered radiation.

As a result of utilizing field stop 75 to block the bottom surface scattered radiation only the top surface scattered radiation is allowed to propagate to de-scan lenses 77 and finally detector 78. As show in FIG. 8, the field stop 75 can be an opaque rectangular object mounted at the focal plane 76 of camera lens 74.

In one example, the optical inspector also includes a processor 80. Processor 80 communicates with either detector 78 or a motor controlling the rate of rotation of rotating polygon 70, or both. In one example, detector 78 communicates a signal indicating the intensity of the light detected by detector 78 to processor 80. The processor 80 then determines if defects are present in the scanned area of the sample based upon the signal received from detector 78. In another example, processor 80 sends a signal to a motor controlling the rotating polygon 70. The signal sent to the motor causes the motor to increase or decrease the rate at which the rotating polygon rotates. The signal sent to the motor may also cause the motor to turn on or turn off.

In one example, the angle of inclination of the camera lens with respect to the plane of incidence of the scanned beam is approximately forty five degrees. The oblique angle of incidence allows the camera lens to separate the scattered radiation from the top and bottom surfaces of the transparent wafer. The amount of separation between the top and bottom surface is determined by the wafer thickness, the angle of incidence, and the index of refraction of the transparent wafer.

FIG. 9 is a diagram of the scan lines at focal plane 46 and 65 of FIG. 6 and FIG. 7, respectively. The top surface scattered radiation scan line is generated from top surface scattered radiation. The bottom surface scattered radiation scan line is generated from the bottom surface scattered radiation.

FIG. 10 is a diagram of the scan lines at focal plane 76 of FIG. 8. The top surface scattered radiation scan line is generated from the top surface scattered radiation. The bottom surface scattered radiation scan line is generated from the bottom surface scattered radiation. Field stop 75 is located at a position along focal plane 76 such that the bottom surface scattered radiation scan line is blocked and the top surface scattered radiation scan line is not blocked. The result of using the field stop 75 in this configuration allows the propagation of the top surface scattered radiation to continue to de-scanning lenses 77 without the contamination of the bottom surface scattered radiation. In one example, field stop 75 is opaque and has an approximately flat upper edge so as to effectively block the the bottom surface scattered radiation while allowing the top surface scattered radiation to pass. The Field stop 75 may be permanently fixed in a given location by a brace or bracket. Alternatively, the field stop 75 may be maneuvered into place by an adjustable means, such as a hinge, mechanical arm, or sliding mechanism.

Figure 11:
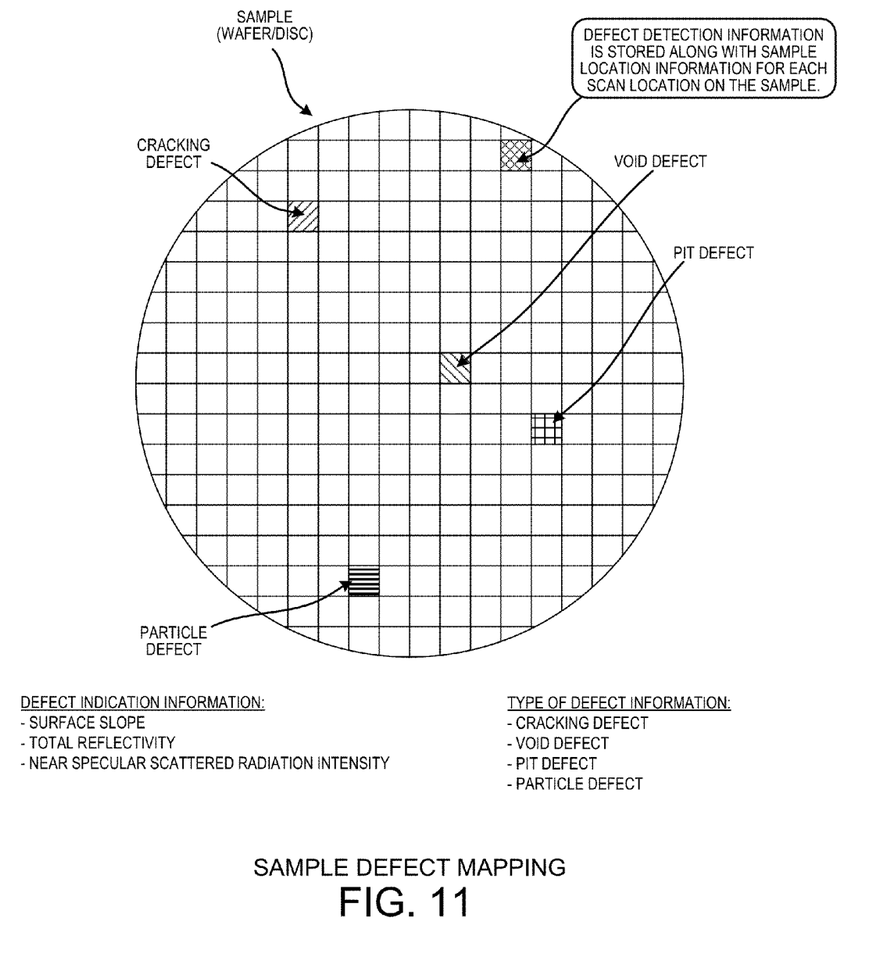
FIG. 11 is a diagram of a sample defect mapping.

FIG. 11 is a diagram of a sample (i.e. wafer or disc) illustrating different scan areas on the surface of the sample. Each scan area is a portion of the sample which is inspected during an optical scan by the optical inspector. The information determined as a result of each optical scan is stored with information location indicating the location on the sample where the optical inspection was performed.

In one example, a processor included in the optical inspector determines whether a defect is present in the current scan location on the sample and records "type of defect information" and the scan location into memory. The type of defect information and scan location information is then read from memory and used to determine which portions of the sample are to be used for production and which parts of the sample are not to be used for production.

In a second example, a processor included in the optical inspector determines various "defect indication information" present in the current scan location on the sample and records the defect indication information (i.e. surface slope, total reflectivity, intensity of scattered radiation) and the scan location information into memory. The determination of type of defect information in the associated scan location is then determined at a post processing stage after the optical scan of the current location is completed. The type of defect information and scan location information are used to determine which portions of the sample are to be used for production and which portions of the sample are not to be used for production. Alternatively, type of defect information may be used to control the sample manufacturing process.

Figure 12:
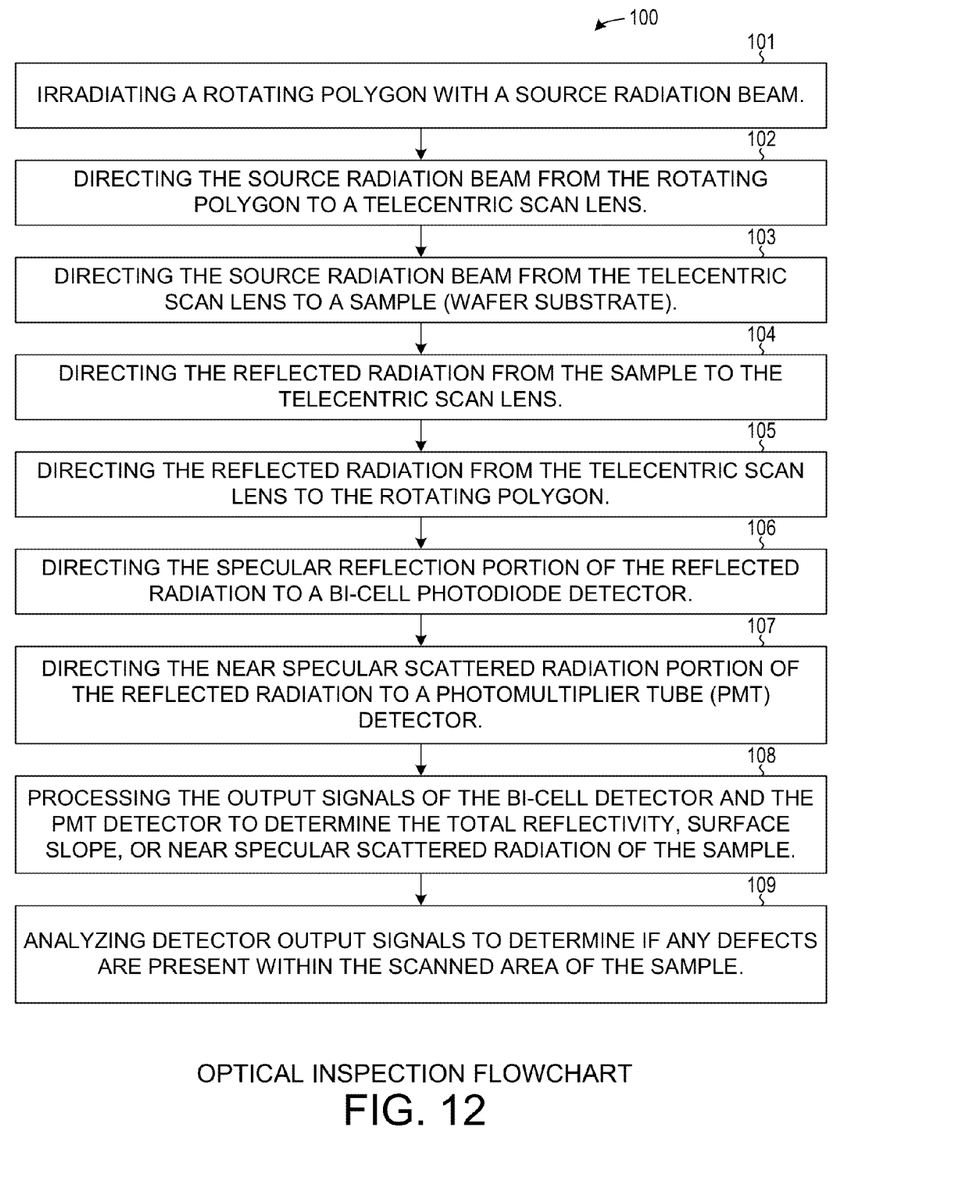
FIG. 12 is a flowchart of steps to determine the total reflectivity, surface slope, and near specular scattered radiation of an irradiated sample.

FIG. 12 is a flowchart 100 of steps to perform optical inspection of a surface. In step 101, a time varying beam reflector (i.e. a rotating polygon) is irradiated with a source radiation beam (i.e. laser). The source radiation beam is directed to telecentric scan lens (Step 102). In step 103, the source radiation beam is directed from the telecentric scan lens to a sample (i.e. wafer or disc). The reflected radiation is directed back to the telecentric scan lens (Step 104). In Step 105, the reflected radiation is directed from the telecentric scan lens to the time varying beam reflector. The specular reflection portion of the reflected radiation is directed to a bi-cell photodiode detector from the time varying beam reflector (Step 106). In step 107, the near specular scattered radiation is directed to a photomultiplier tube (PMT) detector from the time varying beam reflector. In step 108, output signals from the bi-cell detector and the PMT detector are processed to determine the total reflectivity, surface slope, or near specular scattered radiation of the sample. The processor analyzes the reflectivity, surface slope, and near specular scattered radiation to determine the presence of defects on the sample (Step 109).

Figure 13:
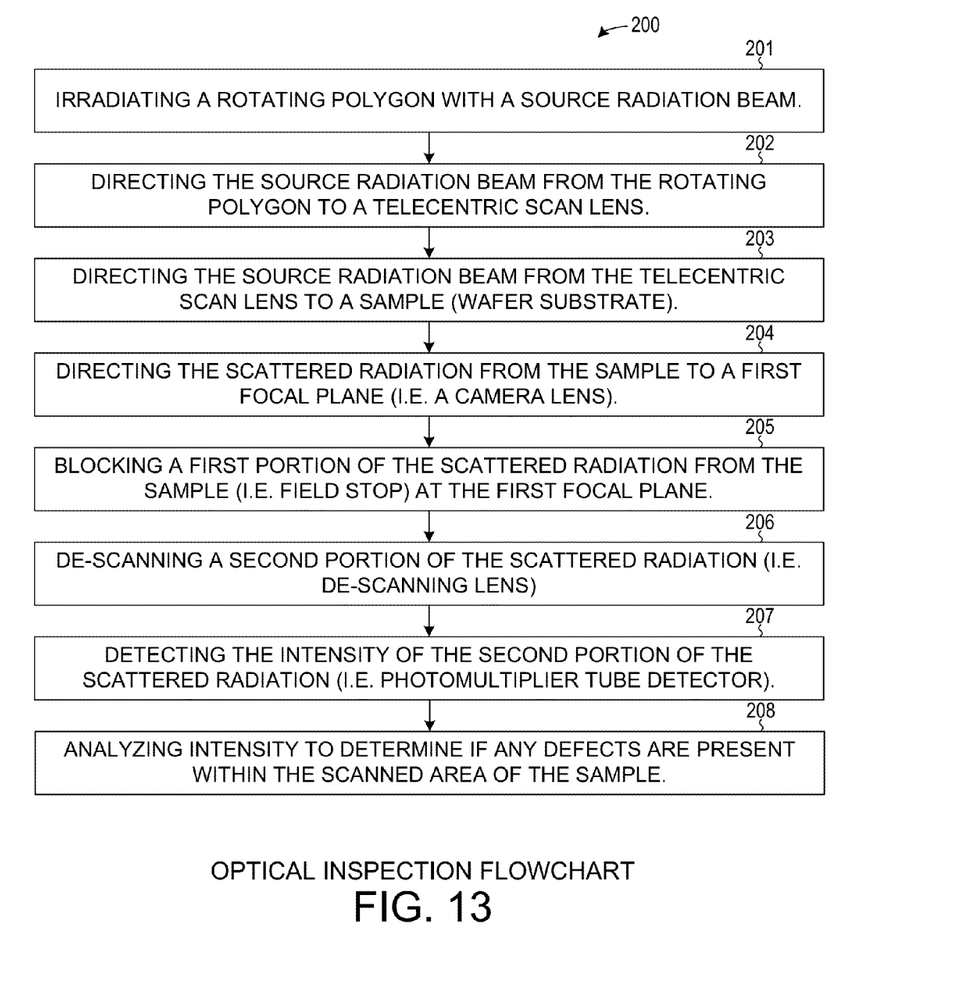
FIG. 13 is a flowchart of steps to determine the intensity of the scattered light of an irradiated sample.

FIG. 13 is a flowchart 200 of steps to perform optical inspection of a surface. In step 201, a time varying beam reflector (i.e. a rotating polygon) is irradiated with a source radiation beam (i.e. laser). The source radiation beam is directed to telecentric scan lens (Step 202). In step 203, the source radiation beam is directed from the telecentric scan lens to a sample (i.e. wafer or disc). The scattered radiation is directed to a first focal plane (i.e. by a camera lens) (Step 204). In Step 205, a first portion of the scattered radiation is blocked at the first focal plane. A second portion of the scattered radiation (not blocked at the first focal plane) is de-scanned (Step 206). In Step 207, detecting the intensity of the de-scanned second portion of the scattered radiation (i.e. by use of a photomultiplier tube detector). The intensity detected by the photomultiplier tube is analyzed to detect the presence of defects on the top surface of the sample (Step 208).

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

The invention claimed is:
1. An apparatus, comprising:
a time varying beam reflector;

a radiating source that irradiates a first position of the time varying beam reflector;

a waveplate that is positioned between the radiating source and the time varying beam reflector;

a telecentric lens that directs the radiation reflected by the time varying beam reflector onto a sample, wherein the radiation reflected by the time varying beam reflector and directed by the telecentric scan lens produces a moving irradiated spot on the sample, wherein the irradiation of the sample causes scattered radiation to reflect from a top surface of the sample and a bottom surface of the sample;

a first lens that receives scattered radiation from the sample, wherein the first lens is orientated at an oblique angle to the plane of incidence of the moving irradiated spot on the transparent sample;

a field stop located at the focal plane of the first lens, wherein the field stop blocks a first portion of the scattered radiation, and wherein a majority of the first portion of scattered radiation is reflected from one surface of the sample;

a de-scan lens located after the focal plane of the first lens that receives a second portion of the scattered radiation not blocked by the field stop; and a detector located at the focal plane of the de-scan lens.

2. The apparatus of claim 1, wherein the time varying beam reflector is a rotating polygon.

3. The apparatus of claim 1, wherein the scattered radiation at the focal plane of the first lens is moving, and wherein the de-scan lens focuses the moving scattered radiation to a stationary location where the detector is located.

4. The apparatus of claim 1, further comprising:

a processor, wherein the processor receives signals from the detector, and wherein the processor determines a characteristic of the sample based upon the signals received from the detector.

5. The apparatus of claim 1, wherein the scattered radiation does not include specular reflection, and wherein the de-scan lens includes one of a pair of achromatic lenses, an aspheric lens, a plano-convex lens, a Cooke triplet lens, or a camera lens.

6. The apparatus of claim 1, wherein the radiating source is a laser, wherein the detector includes a photomultiplier tube, and wherein the sample is a wafer.

7. The apparatus of claim 1, wherein the field stop is not a pinhole field stop.

8. The apparatus of claim 1, further comprising:

a processor; and a motor that drives the time varying beam reflector, wherein the processor communicates with the any combination of: the detector, the radiating source, and the motor.

9. The apparatus of claim 1, wherein the first lens is one of a camera lens, a Cooke triplet lens, a plano-convex lens, an aspheric lens, or an achromatic lens.

10. A method, comprising:

(a) irradiating a first position of a time varying beam reflector;

(b) directing the radiation from the time varying beam reflector onto a sample, wherein the radiation reflected by a time varying beam reflector and directed by the telecentric scan lens produces a moving irradiated spot on the sample, and wherein the irradiation of the sample causes scattered radiation to reflect from a top surface of the sample and a bottom surface of the sample;

(c) focusing scattered radiation from the sample to a first focal plane, wherein the first focal plane is orientated at an oblique angle to the plane of incidence of the moving irradiated spot on the sample;

(d) blocking a first portion of the focused scattered radiation from the sample at the first focal plane, wherein a majority of the first portion of the focused scattered radiation is reflected from one surface of the sample;

(e) de-scanning a second portion of the focused scattered radiation from the sample, wherein the second portion of the focused scattered radiation was not blocked in (d); and (f) detecting the intensity of the second portion of the focused scattered radiation from the sample.

11. The method of claim 10, wherein the irradiating of (a) is performed by a laser source, and wherein the time varying beam reflector is a rotating polygon.

12. The method of claim 10, wherein the focusing of (c) is performed by a camera lens, and wherein the de-scanning of (e) is performed by a pair of achromatic lenses.

13. The method of claim 10, wherein the blocking of (d) is performed by a field stop.

14. The method of claim 10, wherein the detecting of (f) occurs at a second focal plane resulting from the de-scanning of (e).

15. The method of claim 10, wherein the detecting of (f) is performed by a photomultiplier tube.

16. A device comprising:

a time varying beam reflector;

a radiating source that irradiates a first position of the time varying beam reflector;

a waveplate that is positioned between the radiating source and the time varying beam reflector;

a telecentric lens that directs the radiation reflected by the time varying beam reflector onto a sample, wherein the radiation reflected by the time varying beam reflector and directed by the telecentric scan lens produces a moving irradiated spot on the sample, wherein the irradiation of the sample causes scattered radiation to reflect from a top surface of the sample and a bottom surface of the sample;

a first lens that receives scattered radiation from the sample, wherein the first lens is orientated at an oblique angle to the plane of incidence of the moving irradiated spot on the transparent sample; and a first means for blocking a first portion of the scattered radiation from the sample, wherein a majority of the first portion of the scattered radiation is reflected from one surface of the sample; and a second means for de-scanning a second portion of the scattered radiation from the sample.

17. The device of claim 16, wherein the first means includes a field stop, and wherein the second means includes a de-scanning lens.

* * * * *